(12) United States Patent
Jain (10) Patent No.: US 9,135,707 B2
(45) Date of Patent: Sep. 15, 2015

(54) REAL-TIME QUALITY CONTROL OF EM CALIBRATION

(75) Inventor: Ameet Kumar Jain, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 222 days.

(21) Appl. No.: 13/702,724

(22) PCT Filed: May 27, 2011

(86) PCT No.: PCT/IB2011/052328
§ 371 (c)(1),
(2), (4) Date: Mar. 21, 2013

(87) PCT Pub. No.: WO2012/001548
PCT Pub. Date: Jan. 5, 2012

(65) Prior Publication Data
US 2013/0266178 A1   Oct. 10, 2013

Related U.S. Application Data

(60) Provisional application No. 61/358,962, filed on Jun. 28, 2010.

(51) Int. Cl.
*G06K 9/00* (2006.01)
*G06T 7/00* (2006.01)
(Continued)

(52) U.S. Cl.
CPC ............... *G06T 7/004* (2013.01); *A61B 8/4254* (2013.01); *A61B 8/5261* (2013.01);
(Continued)

(58) Field of Classification Search
USPC .................................................. 382/128, 103
See application file for complete search history.

(56) References Cited

U.S. PATENT DOCUMENTS 5,676,673 A   10/1997   Ferre et al.
2002/0062077 A1   5/2002   Emmenegger et al.
(Continued)

FOREIGN PATENT DOCUMENTS

WO   WO2008065600   6/2008
WO   WO2009063360   5/2009

OTHER PUBLICATIONS

Boctor et al., "Real-Time Quality Control of Tracked Ultrasound", Engineering Research Center, johns Hopkins university, USA, US National Library of Medicine National Institutes of Health.
(Continued)

*Primary Examiner* — Vu Le
*Assistant Examiner* — Samah Beg (57) ABSTRACT

A probe (20) generates a plurality of image volumes (13i, 13j) of an anatomical object (10) within a coordinate system (11) and an imaging device (21) generates imaging data (22) representative of the image volumes (13i, 13j) of the anatomical object (10). A position sensor (30) is attached to the probe (20), and a tracking device (31) generates tracking data (22) representative of a tracking of the position sensor (30) within the coordinate system (11). A registration device (40) executes a validation testing of a calibration matrix (51) associated with a spatial relationship between the image volumes (13i, 13j) and the position sensor (30). The validation testing includes a testing of an absolute differential between an image based volume motion (VMIB) and a tracking based volume motion (VMTB) relative to a calibration threshold (CT).

20 Claims, 10 Drawing Sheets (51) Int. Cl.
*A61B 8/00* (2006.01)
*A61B 8/08* (2006.01)
*A61B 19/00* (2006.01)
*G06T 7/20* (2006.01)
*A61B 5/06* (2006.01)
*A61B 5/11* (2006.01)
*A61B 17/00* (2006.01)

(52) U.S. Cl.
CPC .............. *A61B 19/5244* (2013.01); *G06T 7/20* (2013.01); *A61B 5/064* (2013.01); *A61B 5/065* (2013.01); *A61B 5/1113* (2013.01); *A61B 2017/00243* (2013.01); *A61B 2017/00725* (2013.01); *A61B 2019/5251* (2013.01); *A61B 2019/5276* (2013.01); *G06T 2200/04* (2013.01); *G06T 2207/10136* (2013.01); *G06T 2207/30048* (2013.01)

(56) References Cited

U.S. PATENT DOCUMENTS

| | | | |
|---|---|---|---|
| 2004/0019274 A1* | 1/2004 | Galloway et al. | 600/425 |
| 2004/0080467 A1* | 4/2004 | Chinthammit et al. | 345/7 |
| 2004/0097805 A1 | 5/2004 | Verard et al. | |
| 2005/0107687 A1 | 5/2005 | Anderson | |
| 2006/0241432 A1* | 10/2006 | Herline et al. | 600/437 |
| 2006/0258938 A1* | 11/2006 | Hoffman et al. | 600/424 |
| 2007/0034731 A1 | 2/2007 | Falco | |
| 2007/0106156 A1* | 5/2007 | Altmann et al. | 600/437 |
| 2007/0280508 A1* | 12/2007 | Ernst et al. | 382/107 |
| 2008/0269604 A1 | 10/2008 | Boctor et al. | |
| 2008/0276684 A1 | 11/2008 | Goldbach | |
| 2009/0143973 A1* | 6/2009 | Litvin et al. | 701/200 |
| 2009/0171197 A1* | 7/2009 | Burger et al. | 600/426 |
| 2009/0306499 A1* | 12/2009 | Van Vorhis et al. | 600/426 |
| 2010/0066838 A1* | 3/2010 | Steckhan et al. | 348/187 |
| 2011/0134113 A1* | 6/2011 | Ma et al. | 345/419 |
| 2011/0184684 A1* | 7/2011 | Li et al. | 702/94 |
| 2012/0323111 A1* | 12/2012 | Jain et al. | 600/411 |
| 2013/0066196 A1* | 3/2013 | Graumann et al. | 600/424 |
| 2014/0024945 A1* | 1/2014 | Mung et al. | 600/461 |
| 2014/0100452 A1* | 4/2014 | Jain et al. | 600/424 |
| 2014/0121501 A1* | 5/2014 | Fichtinger et al. | 600/424 |
| 2014/0354300 A1* | 12/2014 | Ramachandran et al. | 324/654 |
| 2014/0375822 A1* | 12/2014 | Jain et al. | 348/187 |

OTHER PUBLICATIONS

Boctor et al., Abstract; Source: Med Image Comput Comput Assist interv. 2005; 8 (pt 1):621-630.

* cited by examiner

REAL-TIME QUALITY CONTROL OF EM CALIBRATION

The present invention generally relates to electromagnetic ("EM") tracking of a 3D trans-esophageal echo ("TEE") probe. The present invention specifically relates to real-time quality control of a TEE probe during a minimally invasive intervention.

3D TEE probes are being integrated into routine clinical practice for minimally invasive cardiac therapy, and an EM tracking of the 3D TEE probe inside the body facilitates intra-procedural beating heart surgery and therapy. The EM tracking of a 3D TEE probe requires an accurate calibration between the 3D TEE probe and the EM position sensors, and involves finding a rigid spatial relationship between the voxels in an ultrasound ("US") image and the EM position sensors attached to the 3D TEE probe. The accurate calibration and rigid spatial relationship allows for (a) estimating the motion of the 3D TEE probe as it is moves inside the patient, (b) mapping any TEE volume at any arbitrary time into a common world coordinate system (e.g., coordinate system of an X-ray imager), and (c) helping separate the motion of the 3D TEE probe from that of the heart.

However, the EM tracking of the 3D TEE probe can grow inaccurate for a variety of reasons, including (a) unexpected EM field distortions in the clinical environment (e.g., distortions from the X-ray gantry or a surgical tool), (b) accidental physical movement of the EM position sensors relative to the 3D TEE probe, and (c) partial breakdown of one or more of the EM position sensors. Since the 3D TEE probe is expected to be used for complicated and advanced cardiac procedures, it is important to maintain the calibration between the 3D TEE probe and the EM positions sensors. Specifically, an incorrect calibration can lead to an incorrect motion estimation of the ultrasound volume, leading to an incorrect guidance of the surgical tool. This problem will become particularly critical, as more and more advanced interventional guidance systems are developed with more and more modules fitting into each other. Thus, there is a need for automatic techniques that can continuously monitor, in the background, the accuracy and validity of an interventional guidance system throughout the procedure.

The present invention provides an intra-operative quality control of a probe (e.g., a 3D TEE probe) during a surgical procedure (e.g., a cardiac procedure). Using a calibration method that uses the images being visualized by the probe, the present invention continuously tests the validity of a calibration matrix associated with the probe. If at any point, the calibration matrix becomes invalid for any reason, a warning sign may be raised by the system. This can help the cardiologist either resolve the problem, or switch to another procedure. It will be an easy to use method for the cardiologist to make sure that all the system assumptions are valid, and increase the confidence in the navigation/guidance system.

More particularly, the present invention provides a volume motion-based method to monitor a calibration matrix between image volumes acquired from a probe (e.g., a 3D TEE probe) and tracking data acquired from a position sensor (e.g., an EM position sensor) attached to the probe. The volume motion is measured from two sources, (a) image motion of image volumes and (b) tracking motion of image volumes.

One form of the present invention is an image guided system employing a probe (e.g., a 3D TEE probe), an imaging device (e.g., an ultrasound imaging device), a position sensor (e.g., an electromagnetic sensor) attached to the probe, a tracking device (e.g., an electromagnetic tracking device), and an image-guiding device.

In operation, the probe generates image volumes of an anatomical object (e.g., heart) with each image volume being a distinct subset of a baseline image volume of the anatomical object (e.g., a full US volume scan of a heart, a magnetic resonance imaging of a heart, a computed tomography scan of a heart or a segmented heart model), and the imaging device generates imaging data indicative of the image volumes of the anatomical object. As the probe generates the image volumes, the tracking device tracks the position sensor within a coordinate system and the tracking device generates tracking data indicative of the tracking of the position sensor.

The registration device receives the imaging data from the imaging device and the tracking data from the tracking device for executing a validation testing of a calibration matrix associated with a spatial relationship between the image volumes and the position sensor. The validation testing includes a testing of an absolute differential between an image based volume motion and a tracking based volume motion relative to a calibration threshold. The image based volume motion represents an image motion of the image volumes within the coordinate system derived from the imaging data, and the tracking based volume motion represents a tracking motion of the image volumes within the coordinate system derived from the tracking data.

The foregoing form and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

As previously stated, the present invention provides a motion-based method to validate a calibration matrix between image volumes acquired from a probe (e.g., a 3D TEE probe) and a position sensor (e.g., a EM position sensor) attached to the probe. As will be appreciated by those having ordinary skill in the art from the following descriptions of FIGS. 1-9, the image volume motion is measured from two sources, (a) image motion of image volumes and (b) tracking motion of image volumes.

Figure 1:
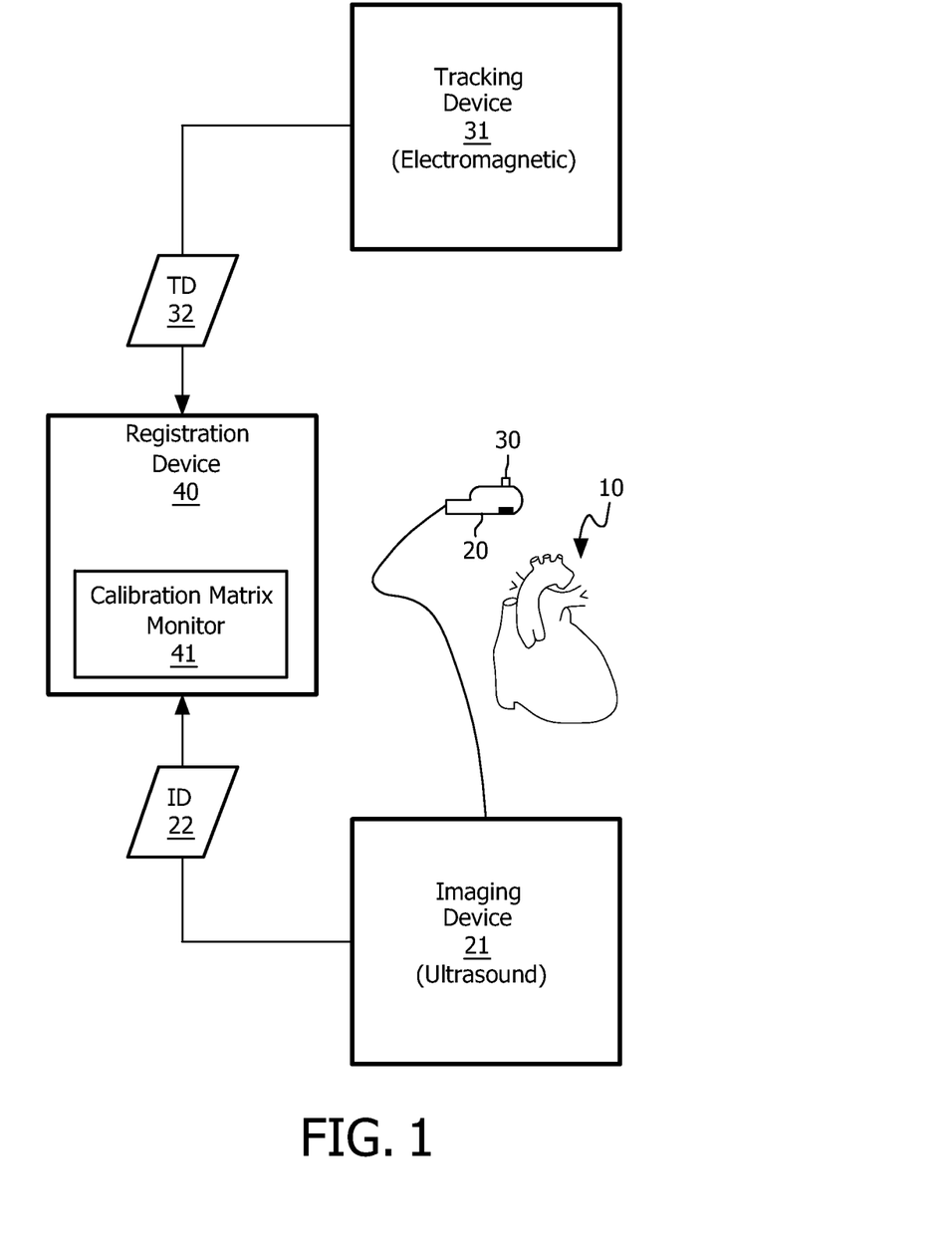
FIG. 1 illustrates an exemplary embodiment of an image-guided system in accordance with present invention.

FIG. 1 illustrates an image-guiding system employing an imaging system, a tracking system and a registration device 40.

For purposes of the present invention, the imaging system is broadly defined herein as any system including a probe 20 structurally configured for generating image volumes of an anatomical object (e.g., a heart 10) within a coordinate system and an imaging device 21 structurally configured for processing the image volumes. Examples of the imaging system include, but are not limited to, any type of ultrasound imaging system, particularly one utilizing a 3D TEE probe. In one embodiment, the iEEE intelligent echo system commercially sold by Philips Healthcare may serve as an ultrasound imaging system.

For purposes of the present invention, the tracking system is broadly defined herein as any system including one or more position sensors 30 attached to probe 20 and a tracking device 31 structurally configured for tracking position sensor(s) 30 within a coordinate system. Examples of the tracking system include, but are not limited to, any type of electromagnetic tracking system and any type of optical tracking system. In one embodiment, the Aurora™ Electromagnetic Tracking System commercially sold by NDI may serve as an electromagnetic tracking system.

For purposes of the present invention, registration device 40 is broadly defined herein as any device structurally configured for registering the image volumes as indicated by imaging data 22 and tracked by probe 30 as indicated by tracking data 32 to a baseline image volume of the anatomical object (e.g., a full US volume of heart 10, a MRI scan of heart 10, a CT scan of heart 10 or a segmented model of heart 10). To this end, a calibration matrix is utilized by registration device 40 as a transformation that coverts the coordinates of the voxels in the image volumes in the coordinate system for tracking position sensor 30, and a calibration monitor 41 of registration device 40 processes imaging data 22 and tracking data 32 for testing the validity of the calibration matrix.

Figure 2:
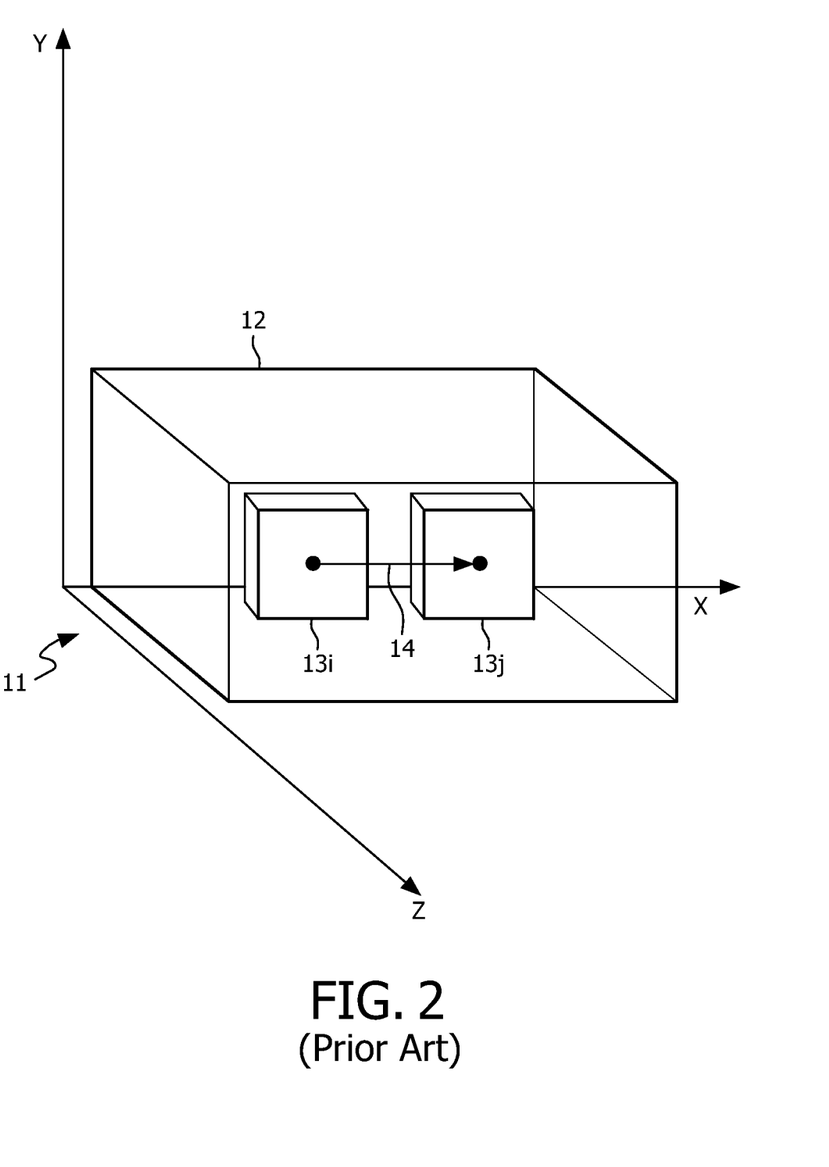
FIG. 2 illustrates an exemplary volume motion of two (2) image volumes of an anatomical object as known in the art.

To facilitate an understanding of the calibration matrix, FIG. 2 illustrates a baseline image volume 12 of an anatomical object (e.g., a full US volume scan of a heart, a MRI scan of a heart, a CT scan of a heart or a segmented heart model) within a coordinate system 11 (e.g., a tracking coordinate system). Probe 20 (FIG. 1) is operated to sequentially generate a volume image 13$i$ and a volume image 13$j$, and position sensor 30 (FIG. 1) is tracked within coordinate system 11 as volume images 13 are generated by probe 20. In practice, volume images 13 may overlap, but are segregated in FIG. 2 for purposes of clearly showing each individual volume image 13.

The calibration matrix provides a transformation that coverts the coordinates of the voxels in image volumes 13 into coordinate system 11. This enables image volumes 13 to be mapped into the coordinate system for image reconstruction purposes. However, the calibration matrix may become inaccurate for a variety of reasons, such as, for example, unexpected field distortions, accidental physical movement of positions sensor 30 relative to probe 20 and a partial breakdown of positions sensor 30. To test the validity of the calibration matrix, calibration monitor 41 measures motion 14 between image volumes 13 from two sources. The first source being an image motion of image volumes 13, and the second source being a tracking motion of image volumes 13.

A description of FIGS. 3-9 will now be provided herein to provide a more detailed explanation of the validity testing of the calibration matrix in accordance with the present invention.

Figure 3:
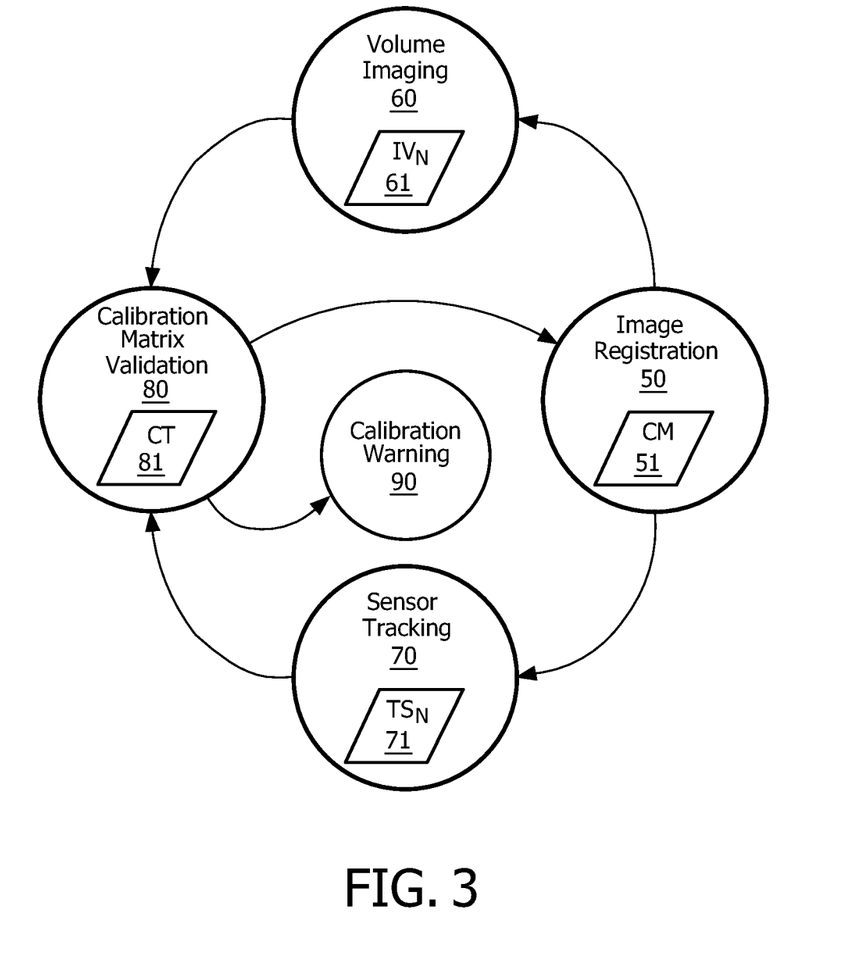
FIG. 3 illustrates an exemplary operation of the imaging guided system in accordance with the present invention.

FIG. 3 illustrates various exemplary operational states of the image-guiding system. Specifically, an image registration state 50 of the system initially involves an acquisition of a baseline image volume of the anatomical object and of a calibration matrix 51 by registration device 40. In practice, calibration matrix 51 may be generated by a geometry phantom based calibration method, an image registration based calibration method or a motion based calibration method as would be known by those having ordinary skill in the art.

The system moves from state 50 to both a volume imaging state 60 for generating a N number of image volumes 61 of the anatomical object (e.g., heart 10) via probe 20 (FIG. 1) and a sensor tracking state 70 for N readings of a tracking signal 71 via position sensor 30 (FIG. 1) with each reading of tracking signal 71 corresponding to a generated image volume 61. The accuracy of calibration matrix 51 is essential for locating each image volume 61 within the coordinate system via tracking signal 71. Thus, a calibration validation state 80 utilizes image volumes 61 and tracking signal 71 to ascertain the validity of the calibration matrix. Specifically, state 80 facilitates the system operating in a loop between states 50-80 for a valid calibration matrix, and conversely, state 80 proceeds to a calibration warning state 90 in view of an invalid calibration matrix. State 80 is implemented by a calibration matrix validation testing method executed by calibration monitor 41 as further explained herein in connection with the description of FIGS. 4-9.

Figure 4:
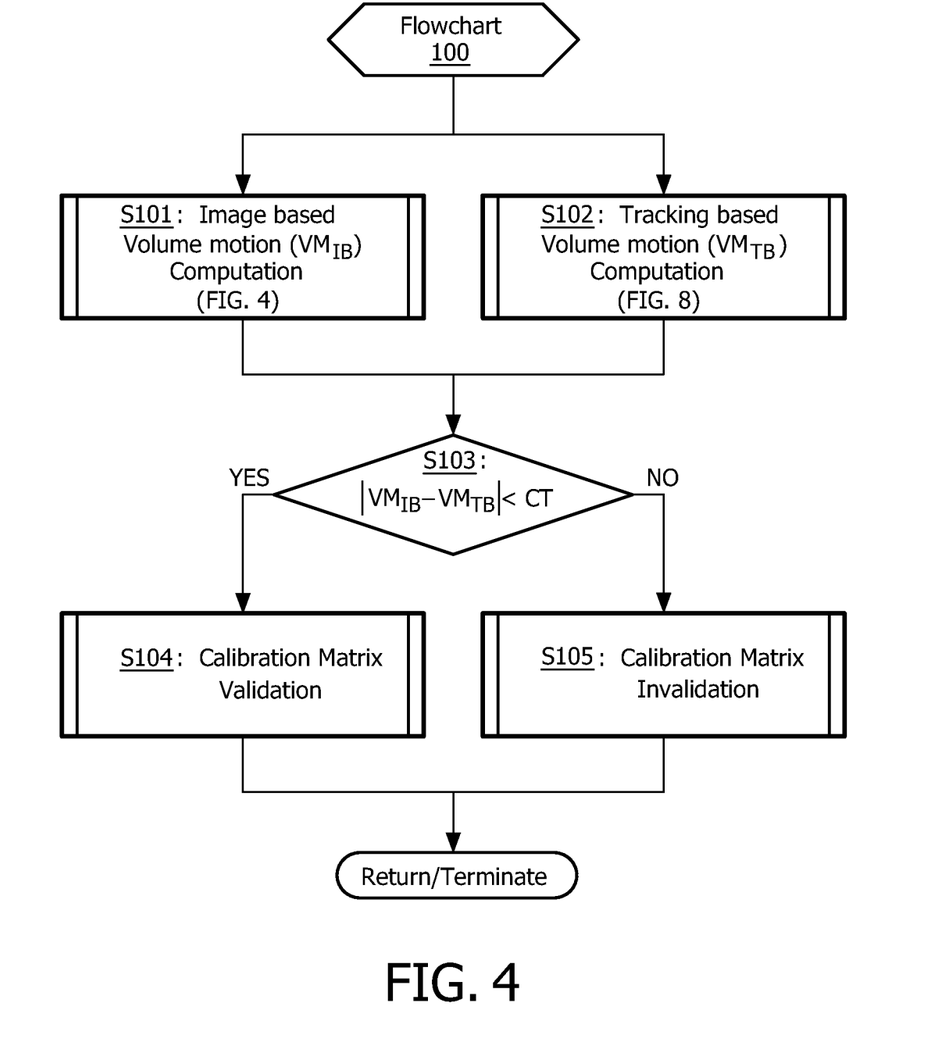
FIG. 4 illustrates a flowchart representative of an exemplary embodiment of a calibration matrix validation testing method in accordance with the present invention.

FIG. 4 illustrates a flowchart 100 representative of one embodiment of the calibration matrix validation testing method. A stage S101 of flowchart 100 encompasses a computation by calibration monitor 41 of an image based volume motion $VM_{IB}$, and a stage S102 of flowchart 100 encompasses a computation by calibration monitor 41 of a tracking based volume motion $VM_{TB}$. For purposes of the present invention, image based volume motion $VM_{IB}$ is broadly defined herein as any motion between image volumes 61 (FIG. 3) of the anatomical object within a coordinate system (e.g., coordinate system 11 shown in FIG. 2) derived from imaging data 22 (FIG. 1) of image volumes 61, and tracking based volume motion $VM_{TB}$ is broadly defined herein as any motion between image volumes 61 of the anatomical object within the coordinate system derived from tracking data 32 (FIG. 1).

Stage S103 of flowchart 100 encompasses a testing of an absolute differential between image based volume motion $VM_{IB}$ and tracking based volume motion $VM_{TB}$ relative to a calibration threshold CT. If the absolute differential is less than calibration threshold CT, then a stage S104 of flowchart 100 encompasses a validation of the calibration matrix that facilitates the continual generation of image volumes 61. Conversely, if the absolute differential is not less than calibration threshold CT, then a stage S105 of flowchart 100 encompasses an invalidation of the calibration matrix that facilitates a warning as to the probable distortion or inaccuracy of image volumes 61.

In one exemplary embodiment of stages S104 and S105, real-time calibration alarm is deactivated as the image volumes 61 are being generated with a valid calibration matrix and is activated as a warning to the probable distortion or inaccuracy of image volumes 61 upon an invalidation of the calibration matrix.

In an exemplary embodiment of stage S105, a regional map of the anatomical object is displayed as a warning to the probable distortion or inaccuracy of image volumes 61 associated with the regional map.

In another exemplary embodiment of stages S104 and S105, a map of the anatomical object may be displayed whereby region(s) of the map associated with an invalid calibration matrix is(are) distinguished from region(s) of the map associated with an valid calibration matrix as a means for providing a warning of probable distortion or inaccuracy of image volumes 61 associated with the invalid region(s).

Figure 5:
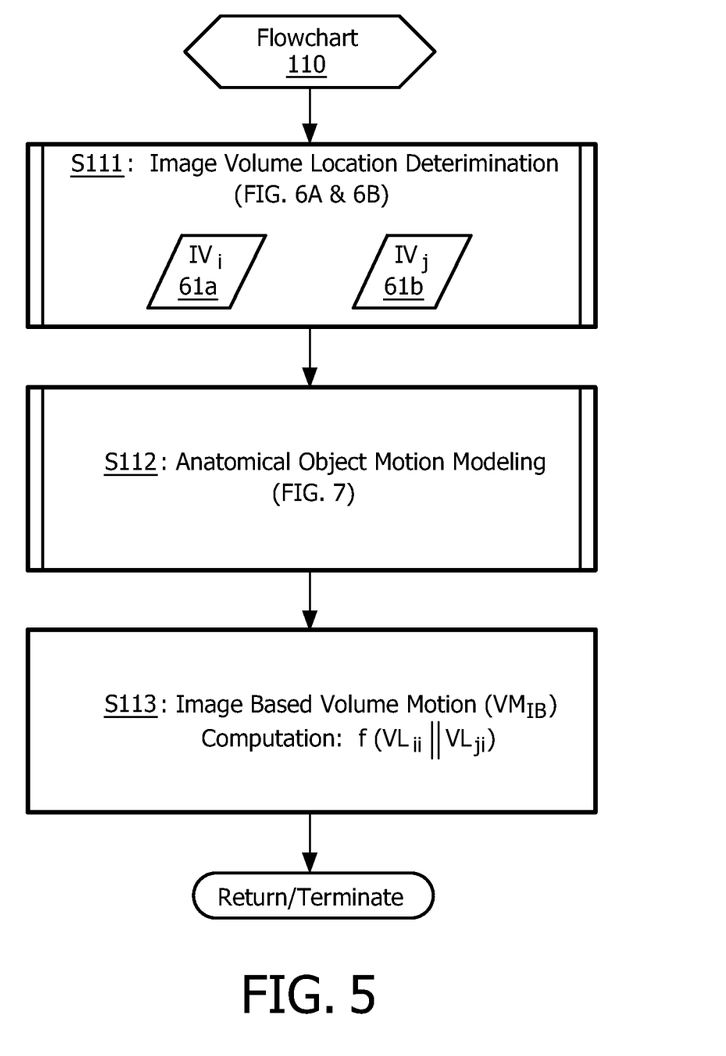
FIG. 5 illustrates a flowchart representative of an exemplary embodiment of an image based volume motion computation method in accordance with the present invention.

FIG. 5 illustrates a flowchart 110 representative of an image based volume motion computation method that may be executed during stage S101 (FIG. 4). This method involves a processing of pair (i,j) of image volumes (e.g., images volumes 13 shown in FIG. 3). Specifically, a stage S111 of flowchart 110 encompasses a determination of a location of an image volume 61a and an image volume 61b within the coordinate system (e.g., system 11 shown in FIG. 3), and a stage S112 of flowchart 110 encompasses a motion compensation of the determined locations of image volumes 61a and 61b in view of a modeling of a motion of the anatomical object (e.g., heart 10).

Figure 6A:
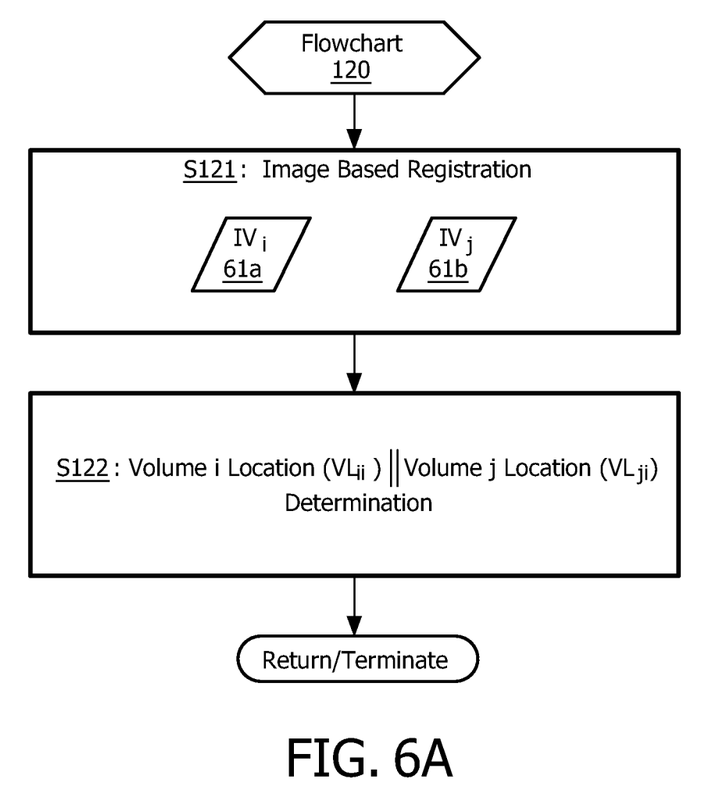
FIGS. 6A and 6B illustrate flowcharts representative of two (2) exemplary embodiments of an image based registration method in accordance with the present invention.

In one embodiment of stage S111 (FIG. 5), a flowchart 120 as shown in FIG. 6A includes a stage S121 encompassing an image based registration of the pair (i,j) of image volumes 61a and 61b via a known image based rigid or deformable registration and known optimization metrics (e.g., mutual information, cross correlation, etc.). Flowchart 120 further includes a stage S122 encompassing a utilization of the registration of image volumes 61a and 61b to determine a location $VL_{ii}$ of image volume 61a within the coordinate system relative to a location $VL_{ji}$ of image volume 61b within the coordinate system.

Figure 6B:
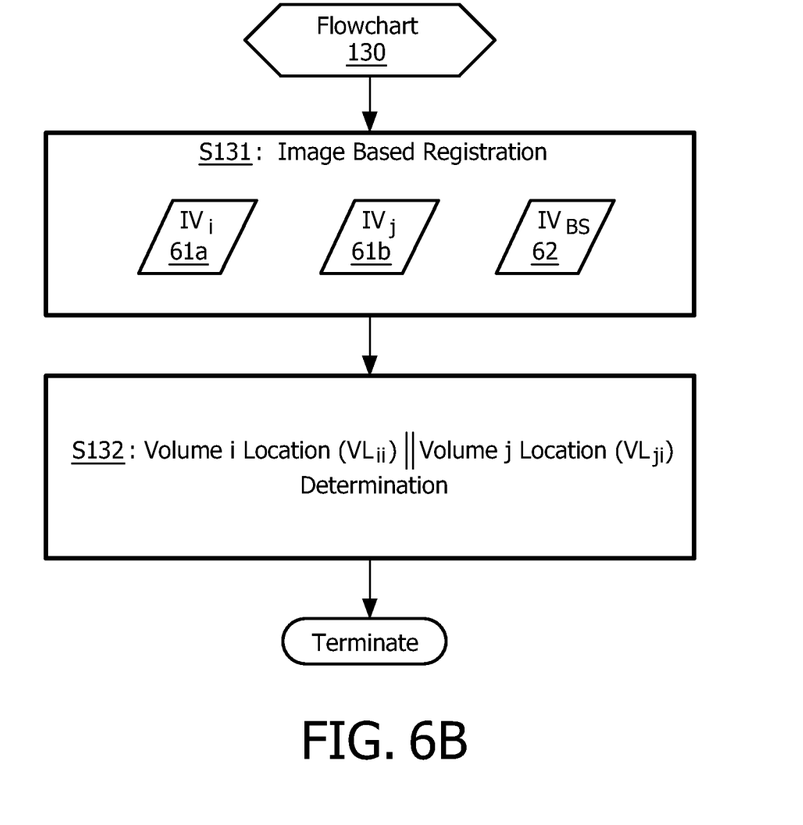

In an alternative embodiment of stage S111 (FIG. 5), a flowchart 130 as shown in FIG. 6B includes a stage S131 encompassing an image based registration of the pair (i,j) of image volumes 61a and 61b to a baseline image volume 62 of the anatomical object (e.g., a full US image, a MRI image, a CT image or a segmented model of the anatomical object). Theses registrations may be performed via an image based rigid or deformable registration and known optimization metrics (e.g., mutual information, cross correlation, etc.). Flowchart 130 further includes a stage S132 encompassing a utilization of the registration of image volume 61a to baseline image volume 62 to determine location $VL_{ii}$ of image volume 61a relative to baseline image volume 62 within the coordinate system. Similarly, the registration of image volume 61b to baseline image volume 62 is utilized to determine a location $V_{ji}$ of image volume 61b relative to the baseline image volume 62 within the coordinate system. This facilitates a determination of location $VL_{ii}$ of image volume 61a relative to location $V_{ji}$ of image volume 61b within the coordinate system.

Figure 7:
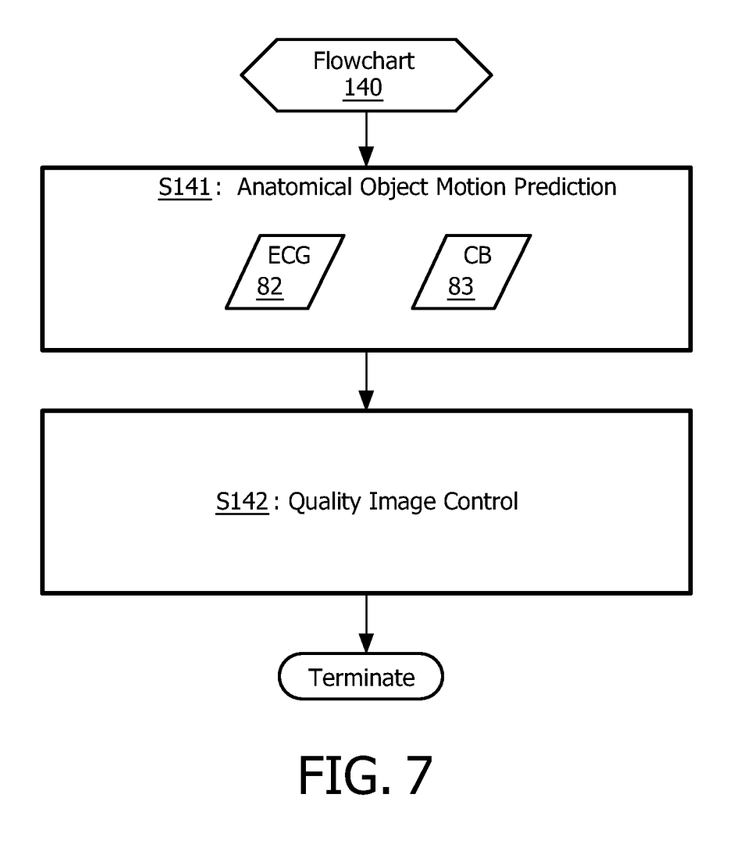
FIG. 7 illustrates a flowchart representative of a first exemplary embodiment of a heart motion modeling method in accordance with the present invention.

In one embodiment of stage S112 (FIG. 5), a flowchart 140 as shown in FIG. 7 include a stage S141 encompassing a prediction of the motion of anatomical object within the coordinate system. For example, with the anatomical object being heart 10, a known learning algorithm utilizing an electrocardiogram signal 82 for cardiac phase, a chest belt signal 83 for respiratory phase and any other additional sensing signals to predict the motion of heart 10 within the coordinate system. Flowchart 140 further includes a stage S142 encompassing a quality image control involving a motion compensation of image volumes 61a and 61b via the predicted motion of the anatomical object. In one embodiment with the anatomical objet being heart 10, image volumes 61 corresponding to a diastolic phase of heart 10 via ECG signal 82 are exclusively utilized by stage S113 (FIG. 5) for quality control purposes and stage S103 (FIG. 4) will only process the volume motions of these selected image volumes 61. Please note this selection assume respiratory motion is minimal.

In an alternative embodiment, image volumes 61 at time intervals when respiratory phase and cardiac phase come back to the same cycle are exclusively utilized by stage S113 (FIG. 5) for quality control purposes and stage S103 (FIG. 4) will only process the volume motions of these selected image volumes 61.

Referring back to FIG. 5, a stage S113 of flowchart 110 encompasses a computation of an image based volume motion $VM_{IB}$ as a function of the location $VL_{ii}$ of image volume 61a within the coordinate system relative to the location $VL_{ji}$ of image volume 61b within the coordinate system as known in the art. The computed image based volume motion $VM_{IB}$ is implemented by stage S103 (FIG. 4) during the testing of the calibration matrix.

Figure 8:
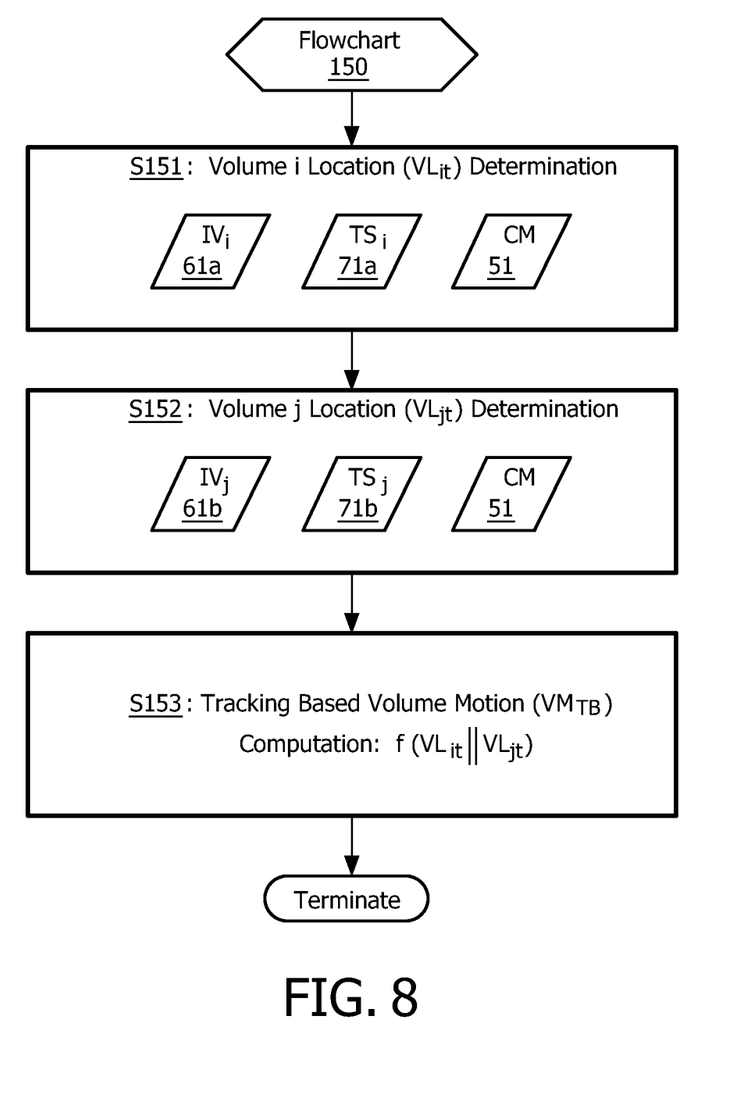
FIG. 8 illustrates a flowchart representative of an exemplary embodiment of a tracking based volume motion computation method in accordance with the present invention.

FIG. 8 illustrates a flowchart 150 representative a tracking based volume motion computation method that may be executed during stage S102 (FIG. 4). A stage S151 of flowchart 150 encompasses a determination of a location $VL_{it}$ of image volume 61a within the coordinate system via a tracking signal 71a and calibration matrix 51 as known in the art. The determined location of $VL_{it}$ of image volume 61a may be confirmed with a location of the baseline image volume of the anatomical object.

A stage S152 of flowchart 150 encompasses a determination of a location $VL_{jt}$ of image volume 61b within the coordinate system via a tracking signal 71b and calibration matrix 51 as known in the art. The determined location of $VL_{jt}$ of image volume 61b may be confirmed with a location of the baseline image volume of the anatomical object.

A stage S153 of flowchart 150 encompasses a computation of the tracking based volume motion $VM_{TB}$ as a function of location $VL_{it}$ of image volume 61a within the coordinate system relative to a location $VL_{jt}$ of volume 61b within the coordinate system as known in the art. In one embodiment, a registration transformation between image volumes 61a and 61b based on location $VL_{it}$ of image volume 61a, location $VL_{jt}$ of volume 61b and calibration matrix 51 may be executed as known in the art during stage S153. This computed tracking based volume motion $VM_{TB}$ is implemented by stage S103 (FIG. 4) during the testing of the calibration matrix.

Figure 9:
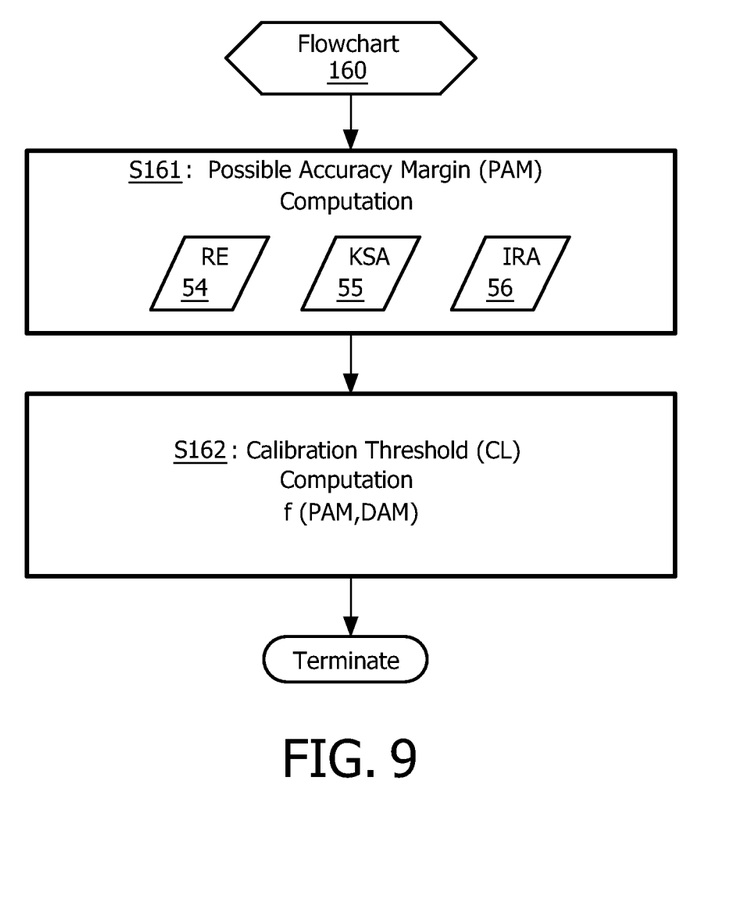
FIG. 9 illustrates a flowchart representative of an exemplary embodiment of a calibration threshold computation method in accordance with the present invention.

FIG. 9 illustrates a flowchart 160 representative of a calibration threshold computation method of the present invention. A stage S161 of flowchart 160 encompasses a computation of a possible accuracy margin of the calibration matrix. In one embodiment, random error information 54 associated with the tracking system, known statistical accuracy data 55 associated with a pre-operative calibration process, and an image registration accuracy data 56 may be utilized in computing the possible accuracy margin.

A stage S162 of flowchart 160 encompasses a computation of calibration threshold CL as a function of the computed possible accuracy margin and a desired accuracy margin associated with the application of the system.

From the description of FIGS. 1-9, those having skill in the art will have a further appreciation on how to implement a validity testing of a calibration matrix for any application in accordance with the present invention.

In practice, calibration matrix 41 may be implemented as software, firmware and/or hardware. Further, in practice, any number of imaging device 21, tracking device 31 and registration device 40 may be integrated into a single device.

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An image-guided system, comprising:
a probe operable to generate a plurality of image volumes of an anatomical object, each image volume being a distinct subset of a baseline image volume of the anatomical object;
an imaging device operable to generate imaging data indicative of the image volumes of the anatomical object;
a position sensor attached to the probe;
a tracking device operable to generate tracking data representative of a tracking of the position sensor within a coordinate system; and
a registration device responsive to the imaging data and the tracking data for executing, during an image-guided procedure, a validation testing of a calibration matrix associated with a spatial relationship between the image volumes and the position sensor,
wherein the validation testing includes a testing of an absolute differential between an image based volume motion and a tracking based volume motion relative to a calibration threshold,
wherein the image based volume motion represents an image motion of the image volumes within the coordinate system derived from imaging data, and
wherein the tracking based volume motion represents a tracking motion of the image volumes within the coordinate system derived from tracking data.

2. The image-guided system of claim 1, wherein the probe is an ultrasound probe and the imaging device is an ultrasound imaging device.

3. The image-guided system of claim 1, wherein the position sensor is an electromagnetic sensor and the tracking device is an electromagnetic tracking device.

4. The image-guided system of claim 1, wherein the calibration matrix is deemed valid in response to the absolute differential between the image based volume motion and the tracking based volume motion being less than the calibration threshold.

5. The image-guided system of claim 1, wherein the calibration matrix is deemed invalid in response to the absolute differential between the image based volume motion and the tracking based volume motion being greater than the calibration threshold.

6. The image-guided system of claim 1, wherein the image based volume motion is computed as a function of an image location of a first image volume within the coordinate system relative to an image location of the second image volume within the coordinate system.

7. The image-guided system of claim 6, wherein a computation of the image based volume motion includes a registration between the first image volume and the second image volume.

8. The image-guided system of claim 6, wherein a computation of the image based volume motion includes a registration of the first image volume and the second image volume to the baseline image volume of the anatomical object.

9. The image-guided system of claim 6, wherein the computation of the image based volume motion includes a compensation for movement of the anatomical object within the coordinate system.

10. The image-guided system of claim 1, wherein the tracking based volume motion is computed as a function of a tracked location of a first image volume within the coordinate system as represented by the tracking data and a tracked location of a second image volume within the coordinate system as represented by the tracking data.

11. The image-guided system of claim 10, wherein a computation of the tracking based volume motion includes a registration transformation between first volume image and the second volume image as a function of the tracked location of the first image volume within the coordinate system, the tracked location of the second image volume within the coordinate system and the calibration matrix.

12. The image-guided system of claim 1, wherein the tracking based volume motion is computed as a function of a tracked location of a first image volume within the coordinate system and a tracked location of a second image volume within the coordinate system.

13. An image-guided system, comprising:
a probe operable to generate a plurality of image volumes of an anatomical object within a coordinate system, each image volume being a distinct subset of a baseline image volume of the anatomical object;
a position sensor attached to the probe; and
a registration device for executing, during an image-guided procedure, a validation testing of a calibration matrix associated with a spatial relationship between the image volumes and the position sensor,
wherein the validation testing includes a testing of an absolute differential between an image based volume motion and a tracking based volume motion relative to a calibration threshold,
wherein the image based volume motion represents an image motion of the image volumes within the coordinate system derived from the image volumes, and
wherein the tracking based volume motion represents a tracking motion of the image volumes within the coordinate system derived from a tracking of the position sensor within the coordinate system.

14. The image-guided system of claim 13, wherein the probe is an ultrasound probe and the position sensor is an electromagnetic sensor.

15. The image-guided system of claim 13, wherein the calibration matrix is deemed valid in response to the absolute differential between the image based volume motion and the tracking based volume motion being less than the calibration threshold.

16. The image-guided system of claim 13, wherein the calibration matrix is deemed invalid in response to the absolute differential between the image based volume motion and the tracking based volume motion being greater than the calibration threshold.

17. An image-guided method, comprising:
operating a probe for generating a plurality of image volumes of an anatomical object, each image volume being a distinct subset of a baseline image volume of the anatomical object;
tracking a position sensor within a coordinate system, the position sensor being attached to the probe;

executing, during an image-guided procedure, a validation testing of a calibration matrix associated with a spatial relationship between the image volumes and the position sensor,     wherein the validation testing includes a testing of an absolute differential between an image based volume motion and a tracking based volume motion relative to a calibration threshold,     wherein the image based volume motion represents an image motion of the image volumes within the coordinate system derived from the image volumes, and     wherein the tracking based volume motion represents a tracking motion of the image volumes within the coordinate system derived from the tracking of the position sensor.

18. The image-guided method of claim 17, wherein the calibration matrix is deemed valid in response to the absolute differential between the image based volume motion and the tracking based volume motion being less than the calibration threshold.

19. The image-guided method of claim 17, wherein the calibration matrix is deemed invalid in response to the absolute differential between the image based volume motion and the tracking based volume motion being greater than the calibration threshold.

20. The image-guided method of claim 17, wherein the image based volume motion is computed as a function of an image location of a first image volume within the coordinate system relative to an image location of the second image volume within the coordinate system.

* * * * *